US012168148B2

United States Patent
Jiang et al.

(10) Patent No.: US 12,168,148 B2
(45) Date of Patent: *Dec. 17, 2024

(54) NEUTRON CAPTURE THERAPY SYSTEM

(71) Applicant: NEUBORON THERAPY SYSTEM LTD., Fujian (CN)

(72) Inventors: Tao Jiang, Jiangsu (CN); Wei-lin Chen, Jiangsu (CN)

(73) Assignee: NEUBORON THERAPY SYSTEM LTD., Xiamen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/381,251

(22) Filed: Oct. 18, 2023

(65) Prior Publication Data

US 2024/0066326 A1 Feb. 29, 2024

Related U.S. Application Data

(63) Continuation of application No. 17/470,145, filed on Sep. 9, 2021, now Pat. No. 11,826,583, and a
(Continued)

(30) Foreign Application Priority Data

Mar. 18, 2019 (CN) .......................... 201910214957.9

(51) Int. Cl.
*A61N 5/10* (2006.01)
*G21G 4/02* (2006.01)
(Continued)

(52) U.S. Cl.
CPC ............. *A61N 5/1078* (2013.01); *G21G 4/02* (2013.01); *G21K 5/04* (2013.01); *H05H 3/06* (2013.01);
(Continued)

(58) Field of Classification Search
CPC ............ A61N 5/1078; A61N 2005/109; A61N 2005/1094; A61N 5/1077; A61N 5/103;
(Continued)

(56) References Cited

U.S. PATENT DOCUMENTS 3,211,623 A * 10/1965 Tower ....................... G21C 1/20
976/DIG. 134
4,705,661 A * 11/1987 Cransac .................. G21C 13/00
376/268
(Continued)

FOREIGN PATENT DOCUMENTS

CN 102439667 A 5/2012
CN 102695544 A 9/2012
(Continued)

OTHER PUBLICATIONS

International Search Report of PCT/CN2020/079564, Sep. 30, 2021.

*Primary Examiner* — David A Vanore
(74) *Attorney, Agent, or Firm* — Locke Lord LLP; Tim Tingkang Xia, Esq.

(57) ABSTRACT

A neutron capture therapy system is provided, including a neutron generating device and a beam shaping assembly. The neutron capture therapy system further includes a concrete wall forming a space for accommodating the neutron generating device and the beam shaping assembly and shielding radiations generated by the neutron generating device and the beam shaping assembly. A support module is disposed in the concrete wall, the support module is capable of supporting the beam shaping assembly and is used to adjust the position of the beam shaping assembly, and the support module includes concrete and a reinforcing portion at least partially disposed in the concrete. The neutron capture therapy system designs a locally adjustable support for the beam shaping assembly, so that the beam shaping
(Continued)

assembly can meet the precision requirement, improve the beam quality, and meet an assembly tolerance of the target.

20 Claims, 6 Drawing Sheets

Related U.S. Application Data continuation of application No. PCT/CN2020/079564, filed on Mar. 17, 2020.

(51) Int. Cl.
    *G21K 5/04*          (2006.01)
    *H05H 3/06*          (2006.01)

(52) U.S. Cl.
    CPC    *A61N 2005/109* (2013.01); *A61N 2005/1094* (2013.01)

(58) Field of Classification Search
    CPC ......... A61N 5/1042; A61N 2005/1092; G21G 4/02; G21K 5/04; G21K 5/02; H05H 3/06; G21F 1/042; G21F 3/00
    See application file for complete search history.

(56) References Cited

U.S. PATENT DOCUMENTS

| | | | | |
|---|---|---|---|---|
| 5,583,900 | A | * | 12/1996 | Kasahara ................ C22C 38/58 376/288 |
| 11,826,583 | B2 | * | 11/2023 | Jiang ........................ H05H 3/06 |
| 2004/0254419 | A1 | * | 12/2004 | Wang ...................... A61L 31/18 424/1.11 |
| 2005/0025797 | A1 | * | 2/2005 | Wang ...................... B82Y 25/00 424/422 |
| 2009/0064604 | A1 | * | 3/2009 | Yamaguchi ........... E02D 29/045 52/169.6 |
| 2010/0296618 | A1 | * | 11/2010 | Sejvar ....................... G21F 3/00 376/293 |
| 2012/0261597 | A1 | * | 10/2012 | Graves ...................... G21F 1/00 29/592 |
| 2013/0139727 | A1 | * | 6/2013 | Constantz ........... C04B 16/0641 106/656 |
| 2014/0260034 | A1 | * | 9/2014 | Ciuperca ................. E04C 5/125 52/405.3 |
| 2014/0364677 | A1 | * | 12/2014 | Katayose ................. G21K 1/10 600/1 |
| 2017/0073270 | A1 | * | 3/2017 | Shao .................... B28B 11/245 |
| 2017/0367897 | A1 | * | 12/2017 | Estrada, Jr. ......... A61F 5/05866 |
| 2018/0025799 | A1 | * | 1/2018 | Kim ......................... G21F 1/12 250/515.1 |
| 2018/0071949 | A1 | * | 3/2018 | Giles ...................... B28B 1/001 |
| 2018/0111876 | A1 | * | 4/2018 | Zampini ............. C04B 16/0625 |
| 2018/0258659 | A1 | * | 9/2018 | LeBlanc .................. E04B 7/20 |
| 2021/0146163 | A1 | * | 5/2021 | Jiang .................... A61N 5/1077 |

FOREIGN PATENT DOCUMENTS

| | | |
|---|---|---|
| CN | 107251157 A | 10/2017 |
| CN | 208114946 U | 11/2018 |
| CN | 208355948 U | 1/2019 |
| CN | 208372313 A | 1/2019 |
| EP | 3357536 A1 | 8/2018 |
| JP | 1147399 | 9/1989 |
| JP | 2007240330 A | 9/2007 |
| JP | 2008039453 A | 2/2008 |
| JP | 2014236913 A | 12/2014 |
| WO | 2019047697 A1 | 3/2019 |
| WO | 2020042681 A1 | 3/2020 |

* cited by examiner

NEUTRON CAPTURE THERAPY SYSTEM

CROSS-REFERENCE TO RELATED PATENT APPLICATION

This application is a continuation application of U.S. Application Ser. No. 17/470,145, filed on Sep. 9, 2021, now allowed, which itself is a continuation application of International Application No. PCT/CN2020/079564, filed on Mar. 17, 2020, which claims priority to Chinese Patent Application No. 201910214957.9, filed on Mar. 18, 2019, the disclosures of which are hereby incorporated by reference.

FIELD

The present disclosure relates to a radiation irradiation system, and in particular to a neutron capture therapy system.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

Various radiations are generated during radiotherapy. For example, neutrons and photons of low-energy to high-energy are generated during boron neutron capture therapy. These radiations may cause different degrees of damage to normal human tissues. Therefore, in the field of radiotherapy, how to reduce radiation pollution to the external environment, medical staff or normal tissues of irradiated subjects is an extremely important issue while effective treatment is achieved. A radiotherapy device is usually placed in a building constructed by concrete to isolate the radiation that may be generated by the device. In a general reinforced concrete structure, rebars are activated by neutrons to generate radioactive isotopes with a relatively long half-life. For example, the half-life of Cobalt-60 is 5.27 years, forming radioactive waste with a long decaying time, leading to negative impact on environment and radiation safety.

In addition, to ensure beam quality and improve treatment effectiveness, it is necessary that a center of a high-energy beam tube coincides with a center of a beam shaping assembly as much as possible. However, an engineering allowable deviation is much higher than a precision requirement for the beam shaping assembly, and when the concrete is vibrated and stirred, conventional wooden formworks deform to some extent, which affects cooperation between the target and the beam shaping assembly and neutron quality.

Therefore, it is necessary to propose a new technical solution to resolve the foregoing problem.

SUMMARY

To resolve the foregoing problem, an aspect of the present disclosure provides a support module for supporting a beam shaping assembly, the beam shaping assembly is configured to adjust beam quality of a radiation generated by a radiation generating device, wherein the support module includes concrete and a reinforcing portion at least partially disposed in the concrete The concrete structure may shield neutrons and other radiations that leak in a working process of the neutron capture therapy system. The reinforcing portion disposed in the concrete may increase the rigidity, tensile strength, and bearing capacity. The modular design provides a design of a locally adjustable support for the beam shaping assembly, so that the beam shaping assembly may meet the precision requirement, improve the beam quality, and meet an assembly tolerance of the target.

Implementations of this aspect may include one or more of the following features.

More particularly, elastic modulus of a material of the reinforcing portion is not less than 40 GPa, ultimate strength of the material is not less than 200 MPa, and yield strength of the material is not less than 100 MPa.

More particularly, more than 90% of weight of the material of the reinforcing portion is composed of at least one element of C, H, O, N, Si, Al, Mg, Li, B, Mn, Cu, Zn, S, Ca, and Ti. The material of the reinforcing portion is made of elements having a cross section for hardly acting with neutrons or being activated by neutrons to generate radioactive isotopes with a short half-life. Because the radioactivity derived from neutron activation is relatively low, a secondary radiation dose is appropriately suppressed, and future device dismantlement is facilitated.

More particularly, half-life of radioactive isotopes generated after the reinforcing portion is activated by neutrons is less than 1 year.

More particularly, the reinforcing portion includes formworks and ribs disposed between the formworks, and the formworks are fixedly connected to the ribs.

Further, the formworks include a lower formwork, a left formwork, a right formwork and an annular formwork, wherein the left formwork and the right formwork are respectively disposed on two sides of the lower formwork, and the annular formwork is surrounded by the lower formwork and the left and right formworks; and the ribs include horizontal transverse ribs, horizontal longitudinal ribs, and vertical ribs distributed in the concrete at a preset spacing respectively in a horizontal direction, a vertical direction, and a thickness direction of the concrete.

Further, the horizontal transverse ribs are welded and anchored to the left formwork, the right formwork, and the annular formwork, the vertical ribs are welded and anchored to the lower formwork, the annular formwork, and the horizontal transverse ribs, and the horizontal longitudinal ribs are welded and anchored to the horizontal transverse ribs and the vertical ribs.

Further, an outer wall of the beam shaping assembly fits an inner surface of the annular formwork, and the beam shaping assembly is fixedly connected to the support module, to constrain forward-backward translational freedom and rotational freedom of the beam shaping assembly.

Another aspect of the present disclosure provides a neutron capture therapy system including a neutron generating device, a beam shaping assembly, a concrete wall and the support module mentioned above. The neutron generating device includes an accelerator and a target, wherein a charged particle beam generated by acceleration of the accelerator acts with the target to generate a neutron beam. The beam shaping assembly including: a moderator configured to moderate the neutrons generated from the target to an epithermal neutron energy range, a reflector surrounding the moderator, wherein the reflector directs deviating neutrons back to the moderator to enhance intensity of an epithermal neutron beam, a thermal neutron absorber provided to absorb thermal neutrons to avoid overdosing in superficial normal tissues during treatment, a radiation shield provided to shield leaking neutrons and photons so as to reduce dose to normal tissues in a non-irradiation area, and a beam exit. The concrete wall forming a space for accommodating the neutron generating device and the beam shaping assembly. The support module is disposed in the concrete wall, and the support module is provided to support the beam shaping assembly and adjust the position of the beam shaping assembly. The concrete structure may shield neutrons and other radiations that leak in a working process of the neutron capture therapy system. The reinforcing portion may increase the rigidity, tensile strength, and bearing capacity of the concrete. The support structure is modularized, so that the beam shaping assembly may be adjusted locally to meet the precision requirement, improve the beam quality, and meet an assembly tolerance of the target.

Implementations of this aspect may include one or more of the following features.

Further, the neutron capture therapy system further includes an irradiation room and a charged particle beam generation room, the irradiation room and the charged particle beam generation room are spaces formed by the concrete wall, the neutron capture therapy system includes a treatment table disposed in the irradiation room, an irradiated subject on the treatment table is treated with irradiation of the neutron beam in the irradiation room, the charged particle beam generation room at least partially accommodates the accelerator, and the support module and the beam shaping assembly are at least partially accommodated in a partition wall between the irradiation room and the charged particle beam generation room.

More particularly, the partition wall is provided, on a side close to the irradiation room, with an accommodating groove at least partially accommodating the support module, and is provided, on a side close to the charged particle beam generation room, with a groove for a transmitting tube of the accelerator to pass through, the accommodating groove and the groove run through the partition wall in a transmission direction of the neutron beam, and a cross section contour of the support module is located between cross section contours of the accommodating groove and the groove on a plane perpendicular to the transmission direction of the neutron beam. Therefore, seams are avoided in a beam transmission direction, radiation is further reduced, and the support module is easy to adjust.

More particularly, a shielding plate is disposed on the side of the partition wall close to the irradiation room, and the shielding plate matches a cross section contour of the support module on a plane perpendicular to the transmission direction of the neutron beam. The shielding plate may shield neutrons leaking between the support module and the partition wall, and may also enhance the shielding effect of the partition wall and suppress secondary radiation generated by the partition wall, thereby avoiding radiation on normal tissues of a patient.

More particularly, an adjusting member is disposed on the support module to adjust positions of the support module and the beam shaping assembly, to improve a degree of coincidence between the center of the beam shaping assembly and the center of a beam line, so that the target may be placed in a center hole of the beam shaping assembly.

Further, the beam shaping assembly moves between a first position and a second position, the accelerator comprises a transmitting tube, a center axis of the beam shaping assembly approximately coincides with a center axis of the transmitting tube at the first position, and the center axis of the beam shaping assembly does not coincide with the center axis of the transmitting tube at the second position.

Further, the adjusting member includes a first side plate and a second side plate that are connected to each other, the first side plate is fixedly and detachably connected to the support module, and the second side plate is provided to act on.

Further, a shield is filled between the partition wall and the support module to maintain positions of the support module and the beam shaping assembly, thereby preventing the beam from passing through a gap between the partition wall and the support module, a material of the shield includes at least one of a photon shielding material and a neutron shielding material, and the shield includes at least one of a rigid solid, a flexible solid, a liquid, and a powder.

A third aspect of the present disclosure provides a neutron capture therapy system including a neutron generating device, a beam shaping assembly, a concrete wall, the support module mentioned above, and an adjusting member. The neutron generating device includes an accelerator and a target, wherein a charged particle beam generated by acceleration of the accelerator acts with the target to generate a neutron beam. The beam shaping assembly including: a moderator configured to moderate the neutrons generated from the target to an epithermal neutron energy range, a reflector surrounding the moderator, wherein the reflector directs deviating neutrons back to the moderator to enhance intensity of an epithermal neutron beam, a thermal neutron absorber provided to absorb thermal neutrons to avoid overdosing in superficial normal tissues during treatment, a radiation shield provided to shield leaking neutrons and photons so as to reduce dose to normal tissues in a non-irradiation area, and a beam exit. The concrete wall forming a space for accommodating the neutron generating device and the beam shaping assembly. The support module is disposed in the concrete wall and provided to support the beam shaping assembly. The adjusting member is configured to adjust the position of the beam shaping assembly. The concrete structure may shield neutrons and other radiations that leak in a working process of the neutron capture therapy system. The reinforcing portion may increase the rigidity, tensile strength, and bearing capacity of the concrete. The support structure is modularized, so that the beam shaping assembly may be adjusted locally to meet the precision requirement, improve the beam quality, and meet an assembly tolerance of the target.

Implementations of this aspect may include one or more of the following features.

More particularly, the beam shaping assembly moves between a first position and a second position, the accelerator includes a transmitting tube, a center axis of the beam shaping assembly approximately coincides with a center axis of the transmitting tube at the first position, and the center axis of the beam shaping assembly does not coincide with the center axis of the transmitting tube at the second position.

More particularly, the adjusting member includes a first side plate and a second side plate that are connected to each other, the first side plate is fixedly and detachably connected to the support module or the beam shaping assembly, and the second side plate is provided to act on.

More particularly, the adjusting member is disposed on the support module to adjust positions of the support module and the beam shaping assembly, to improve a degree of coincidence between the center of the beam shaping assembly and the center of a beam line, so that the target may be placed in a center hole of the beam shaping assembly.

Further, a shield is filled between the concrete wall and the support module to maintain positions of the support module and the beam shaping assembly, thereby preventing the beam from passing through a gap between the partition wall and the support module, a material of the shield includes at least one of a photon shielding material and a neutron shielding material, and the shield includes at least one of a rigid solid, a flexible solid, a liquid, and a powder.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

Embodiments of the present invention are further described below in detail with reference to the accompanying drawings, to enable a person skilled in the art to implement the present invention with reference to the text of the specification.

Figure 1:
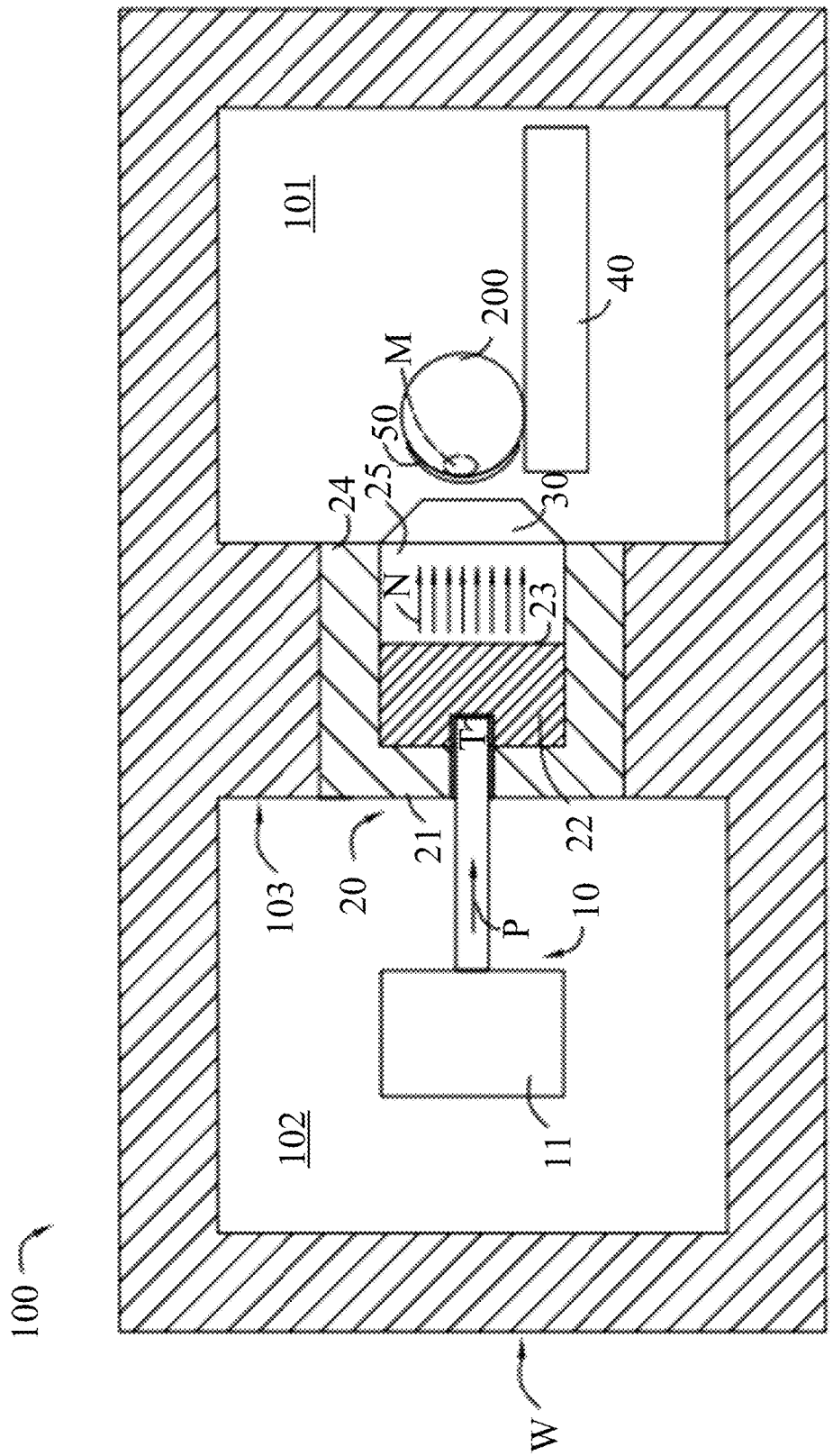
FIG. 1 is a schematic structural diagram of a neutron capture therapy system according to an embodiment of the present disclosure.

As shown in FIG. 1, a neutron capture therapy system in this embodiment is preferably a boron neutron capture therapy system 100, which includes a neutron generating device 10, a beam shaping assembly 20, a collimator 30, and a treatment table 40. The neutron generating device 10 includes an accelerator 11 and a target T, and the accelerator 11 accelerates charged particles (such as protons, deuterons, etc.) to generate a charged particle beam P such as a proton beam, and the charged particle beam P irradiates the target T and interacts with the target T to generate a neutron beam N, and the target T is a metal target. Suitable nuclear reactions are always determined according to such characteristics as desired neutron yield and energy, available accelerated charged particle energy and current and materialization of the metal target, among which the most discussed two are $^7$Li (p, n) $^7$Be and $^9$Be (p, n) $^9$B and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions. The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. The target in these embodiments of the present disclosure is made of lithium. However, well known by those skilled in the art, the target materials may be made of other metals besides lithium or beryllium, for example, tantalum (Ta) or tungsten (W). The target T may be in the shape of a disk, or may be in other solid shapes, or a liquid (liquid metal) may be used. The accelerator 11 may be a linear accelerator, a cyclotron, a synchrotron, a synchrocyclotron, and the neutron generating device 10 may also be a nuclear reactor without using an accelerator and a target. No matter BNCT neutron sources are from the nuclear reactor or the nuclear reactions between the accelerator charged particles and the target, only mixed radiation fields are produced, that is, beams include neutrons and photons having energies from low to high. As for BNCT of deep tumors, except the epithermal neutrons, the more the residual quantity of radiation ray is, the higher the proportion of nonselective dose deposition in the normal tissue is. Therefore, radiation causing unnecessary dose should be lowered down as much as possible. In addition, for the normal tissues of the irradiated subject, too much various radiations should be avoided, which also causes unnecessary dose deposition.

The neutron beam N generated by the neutron generating device 10 sequentially passes through the beam shaping assembly 20 and the collimator 30 and then irradiates to the irradiated subject 200 on the treatment table 40. The beam shaping assembly 20 is capable of adjusting the beam quality of the neutron beam N generated by the neutron generating device 10, and the collimator 30 is used to concentrate the neutron beam N, so that the neutron beam N has higher targeting during the treatment process. By adjusting the collimator 30, the direction of the beam and the positional relationship of the beam and the irradiated subject 200 on the treatment table 40 can be adjusted, and the position of the treatment table 40 and the irradiated subject 200 can also be adjusted to align the beam with the tumor cells M in the irradiated subject 200. These adjustments can be performed manually or automatically through a series of control mechanisms. It will be appreciated that the present disclosure may also be provided without a collimator, and the beam from the beam shaping assembly 20 directly irradiates to the irradiated subject 200 on the treatment table 40.

The beam shaping assembly 20 further includes a reflector 21, a moderator 22, a thermal neutron absorber 23, a radiation shield 24, and a beam exit 25. The neutrons generated by the neutron generating device 10 have a wide spectrum of energy, and in addition to epithermal neutrons to meet treatment needs, it is desirable to reduce other types of neutrons and photons as much as possible to avoid injury to operators or patients. Therefore, the neutrons from the neutron generating device 10 need to pass through the moderator 22 to moderate the energy (>40 keV) of fast neutrons into an epithermal neutron energy range (0.5 eV to 40 keV) and reduce thermal neutrons (<0.5 eV) as much possible. The moderator 22 is made of a material having a cross section for principally acting with fast neutrons but hardly acting with epithermal neutrons. In this embodiment, the moderator 13 is made of at least one of $D_2O$, $A_1F_3$, Fluental, $CaF_2$, $Li_2CO_3$, $MgF_2$ and $Al_2O_3$. The reflector 21 surrounds the moderator 22, and directs the neutrons diffused through the moderator 22 back to the neutron beam N to improve the utilization of the neutrons, and is made of a material having high neutron reflection ability. In this embodiment, the reflector 21 is made of at least one of Pb or Ni. A thermal neutron absorber 23, which is made of a material having a large cross section for acting with thermal neutrons, is at the rear of the moderator 22. In this embodiment, the thermal neutron absorber 23 is made of Li-6. The thermal neutron absorber 23 is configured to absorb the thermal neutrons passing through the moderator 22 to reduce the content of thermal neutrons in the neutron beam N, thereby avoiding overdosing in superficial normal tissues during treatment. A radiation shield 24 is configured to shield neutrons and photons that leak from portions other than the beam exit 25. The material of the radiation shield 24 includes at least one of a photon shielding material and a neutron shielding material. In this embodiment, the material of the radiation shield 24 includes a photon shielding material lead (Pb) and a neutron shielding material polyethylene (PE). The collimator 30 is disposed at the rear of the beam exit 25, and the epithermal neutron beam emerging from the collimator 30 irradiates to the irradiated subject 200, and is slowed into thermal neutrons to reach the tumor cell M after passing through the superficial normal tissue. It will be appreciated that the beam shaping assembly 20 may have other configurations as long as the epithermal neutron beam required for treatment can be obtained.

After the irradiated subject 200 is administrated or injected boron (B-10)-containing pharmaceuticals, the boron-containing pharmaceuticals selectively accumulates in the tumor cell M, and then takes advantage that the boron (B-10)-containing pharmaceuticals have high neutron capture cross section and produces 4 He and $^7$Li heavy charged particles through $^{10}B(n, \alpha)$ $^7$Li neutron capture and nuclear fission reaction. The two charged particles, with average energy at about 2.33 MeV, are of high linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level. only the tumor cells will be destroyed on the premise of having no major normal tissue damage.

In this embodiment, a radiation shielding device 50 is further disposed between the irradiated subject 200 and the beam exit 25 to shield normal tissue of the irradiated subject from irradiation by the beam from the beam exit 25. It should be understood that the radiation shielding device 50 may not be disposed.

The boron neutron capture therapy system 100 as a whole is completely accommodated in a building constructed by concrete. Specifically, the boron neutron capture therapy system 100 further includes an irradiation room 101 and a charged particle beam generation room 102. The irradiated subject 200 on the treatment table 40 is treated by irradiation with the neutron beam N in the irradiation room 101. The charged particle beam generation room 102 at least partially accommodates the accelerator 11. The beam shaping assembly 20 is at least partially accommodated in a partition wall 103 between the irradiation room 101 and the charged particle beam generation room 102. It may be understood that the partition wall 103 may completely separate the irradiation room 101 from the charged particle beam generation room 102. Alternatively, the partition wall 103 may partially separate the irradiation room 101 from charged particle beam generation room 102, and the irradiation room 101 is in communication with the charged particle beam generation room 102. There may be one or more targets T. The charged particle beam P may selectively act with one or several targets T or may simultaneously act with a plurality of targets T, to generate one or more therapeutic neutron beams N. Corresponding to the quantity of the targets T, there may also be one or more beam shaping assemblies 20, collimators 30, and treatment tables 40. A plurality of treatment tables may be disposed in the same irradiation room, or an individual irradiation room may be disposed for each treatment table.

Figure 2:
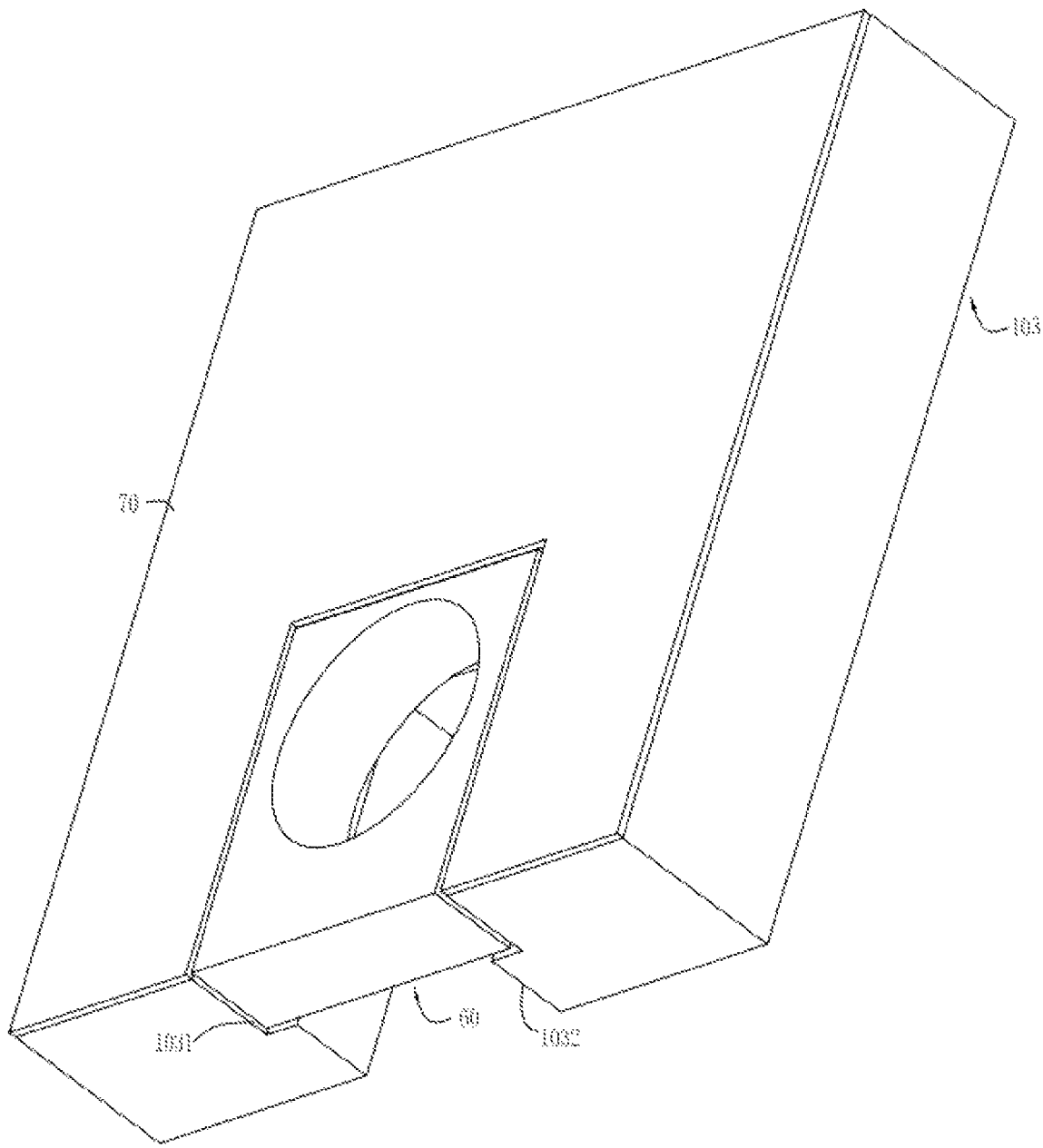
FIG. 2 is a schematic diagram of mounting of a support module of a beam shaping assembly of a neutron capture therapy system according to an embodiment of the present disclosure.

The irradiation room 101 and the charged particle beam generation room 102 are spaces defined by a concrete wall W (including the partition wall 103). The concrete structure may shield leaking neutrons and other radiations in a working process of the boron neutron capture therapy system 100. Referring to FIG. 2, the beam shaping assembly 20 is supported by a support module 60 disposed in the partition wall 103. The partition wall 103 is provided, on a side close to the irradiation room 102, with an accommodating groove 1031 at least partially accommodating the support module 60, and is provided, on a side close to the charged particle beam generation room 101, with a groove 1032 for a transmitting tube of the accelerator to pass through, so that the accommodating groove 1031 and the groove 1032 run through the partition wall in a transmission direction of the neutron beam N. In this embodiment, a wall surface of the partition wall 103 is a plane, and the transmission direction of the neutron beam N is perpendicular to the wall surface of the partition wall 103. The support structure is modularized, so that the beam shaping assembly can be adjusted locally to meet the precision requirement, improve the beam quality, and meet an assembly tolerance of the target. A cross section contour of the support module 60 is located between cross section contours of the accommodating groove 1031 and the groove 1032 on a plane perpendicular to the transmission direction of the neutron beam N, so that seams are avoided in a beam transmission direction, radiation is further reduced, and in addition, the support module 60 is easy to adjust. In this embodiment, the support module 60 is a cuboid as a whole, cross sections, perpendicular to the transmission direction of the neutron beam N, of the accommodating groove 1031 and the groove 1032 are both in a "u" shape, and side walls of the accommodating groove 1031 and the groove 1032 are parallel to the transmission direction of the neutron beam N. A shielding plate 70 is further disposed on the side of the partition wall 103 close to the irradiation room 102. The shielding plate 70 can enhance the shielding effect of the partition wall and suppress secondary radiation generated by the partition wall, thereby avoiding radiation on normal tissues of a patient. The shielding plate 70 may match the cross section contour of the support module 60 on the plane perpendicular to the transmission direction of the neutron beam N, thereby shielding neutrons leaking between the support module and the partition wall. The shielding plate is a PE plate. It may be understood that the shielding plate may also be disposed on the side of the partition wall 103 close to the charged particle beam generation room 102 and a side of the support module 60 close to the irradiation room 101. The shielding plate may be made of lead or another neutron or photon shielding material. Alternatively, the shielding plate may be omitted.

Figure 3:
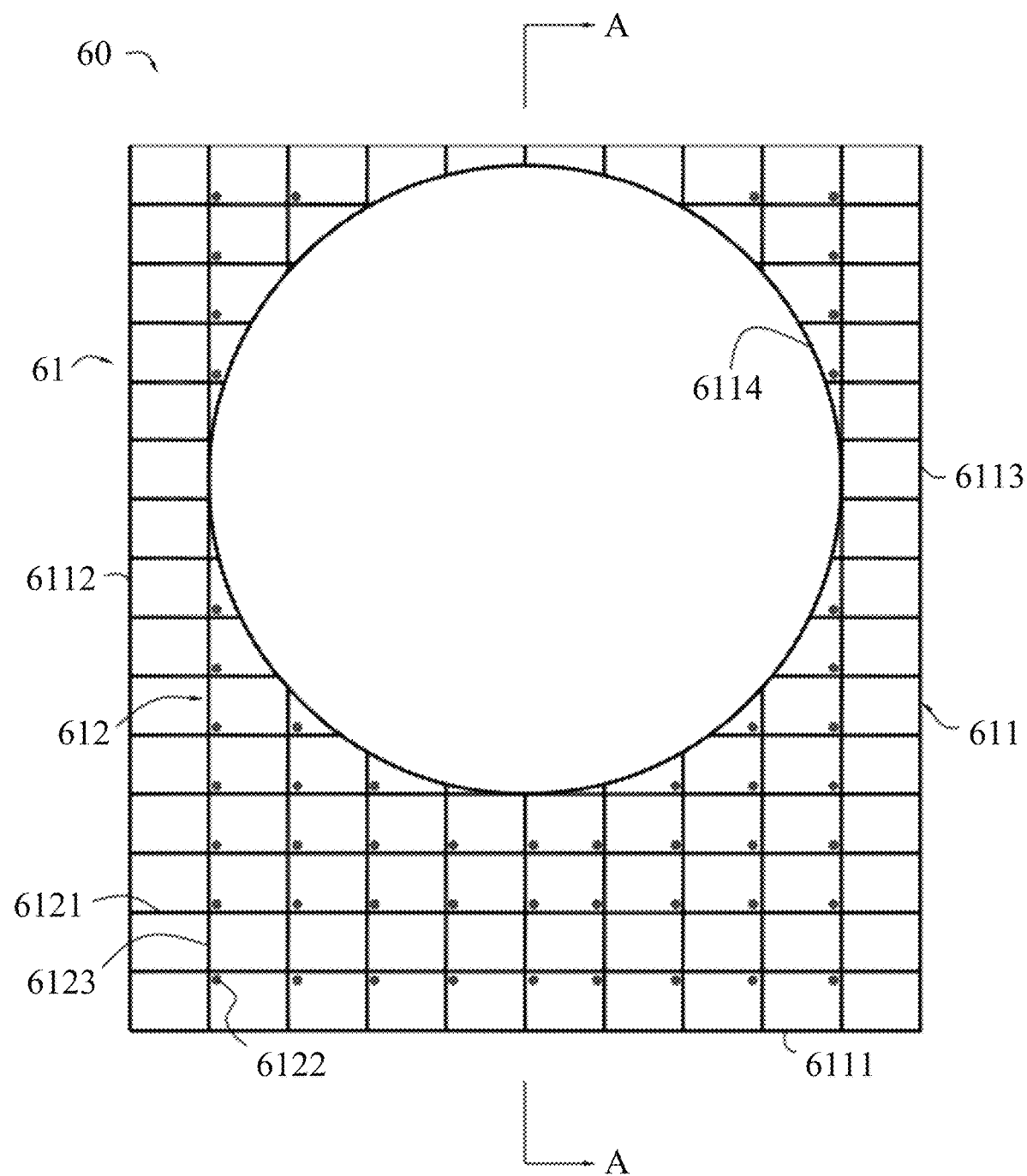
FIG. 3 is a schematic structural diagram of the support module of the beam shaping assembly in FIG. 2.
Figure 4:
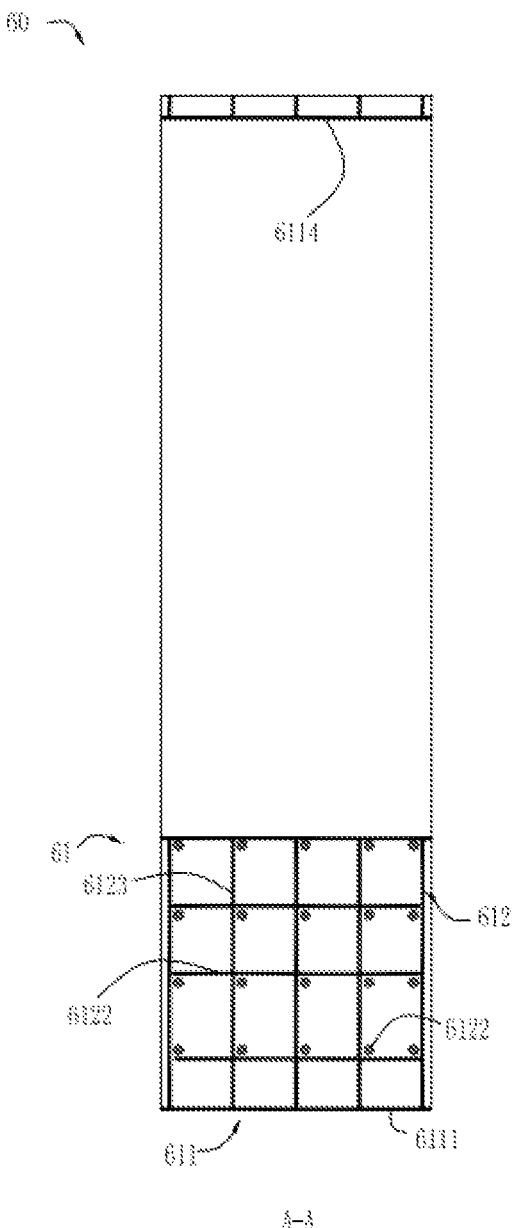
FIG. 4 is a schematic sectional view along A-A in FIG. 3.

Referring to FIG. 3 and FIG. 4, the support module 60 includes concrete and a reinforcing portion 61 at least partially disposed in the concrete (described in detail below). The concrete has low tensile strength and is easy to crack, and the beam shaping assembly is very sensitive to deformation and requires that the support structure has sufficient stiffness. Therefore, the reinforcing portion disposed in the concrete may increase the rigidity, tensile strength, and bearing capacity. Elastic modulus of a material of the reinforcing portion is not less than 40 GPa, ultimate strength of the material is not less than 200 MPa, and yield strength of the material is not less than 100 MPa. Because neutrons are generated in the beam shaping assembly, the surrounding material is most severely activated. The material of the reinforcing portion is made of elements having a cross section for hardly acting with neutrons or being activated by neutrons to generate radioactive isotopes with a short half-life (less than 1 year). For example, more than 90% of weight of the material of the reinforcing portion is composed of at least one of C, H, O, N, Si, Al, Mg, Li, B, Mn, Cu, Zn, S, Ca, and Ti. In this embodiment, at least partial material of the reinforcing portion is an aluminum alloy. The half-life of aluminum activated by neutrons is relatively short, and is only 2.2 minutes. In a conventional reinforced concrete structure, elements, such as iron, cobalt, and nickel, abundantly contained in the rebars have relatively long half-lives after being activated by neutrons. For example, the half-life of Cobalt-60 is 5.27 years. If the aluminum alloy is used, because the radioactivity derived from neutron activation is greatly reduced within a limited time, a secondary radiation dose is appropriately suppressed, and future device dismantlement is facilitated. The material of the reinforcing portion may be further an aluminum-magnesium alloy, or may be a carbon fiber composite material, a glass fiber composite material, or a combination thereof.

The reinforcing portion 61 includes formworks 611 and ribs 612 disposed between the formworks, and the formworks 611 are fixedly connected to the ribs 612. The formworks 611 include a lower formwork 6111, a left formwork 6112 and a right formwork 6113 that are respectively disposed on two sides of the lower formwork 6111, and an annular formwork 6114 surrounded by the lower formwork and the left and right formworks. The formworks 611 are made of an aluminum alloy and are used as anchor plates for the ribs 612. In this embodiment, the beam shaping assembly 20 is cylindrical as a whole. It may be understood that, when the beam shaping assembly is constructed into another shape, the annular formwork may be replaced with a formwork of another shape correspondingly. The ribs 612 include horizontal transverse ribs 6121, horizontal longitudinal ribs 6122, and vertical ribs 6123 distributed in the concrete among the annular formwork, the left and right formworks, and the lower formwork at a preset spacing respectively in a horizontal direction, a vertical direction, and a thickness direction of the concrete. The spacing is determined according to a specific case, and is schematically drawn in the figures. The ribs are also made of an aluminum alloy. In this embodiment, the horizontal transverse ribs 6121 are welded and anchored to the left formwork 6112, the right formwork 6113, and the annular formwork 6114, the vertical ribs 6123 are welded and anchored to the lower formwork 6111, the annular formwork 6114, and the horizontal transverse ribs 6121, and the horizontal longitudinal ribs 6122 are welded and anchored to the horizontal transverse ribs 6121 and the vertical ribs 6123. It may be understood that the formworks and the ribs may alternatively be disposed in another manner. A welding sequence and process may be carried out in another manner well known to a person skilled in the art, or another fixing manner may be used.

During construction, front and rear formworks (not shown in the figure) also need to be set up. Front and rear sides and an upper side of the support module 60 do not need to be anchored, so that conventional wooden formworks are used. Concrete is poured into an accommodating cavity formed among the lower formwork 6111, the left formwork 6112, the right formwork 6113, the annular formwork 6114, and the front and rear formworks. No formwork is disposed on an upper side, so that a status of the concrete can be conveniently observed during the construction. After the concrete is filled up, an upper side thereof may be leveled with a plate. After the concrete is poured and cured, the front and rear formworks are removed to form the support module 60, and then the support module 60 is delivered to the partition wall 103 and mounted in the accommodating groove 1031. Next, the beam shaping assembly 20 is placed in the support module 60, and an outer wall of the beam shaping assembly 20 fits an inner surface of the annular formwork 6114. To constrain forward-backward translational freedom and rotational freedom of the beam shaping assembly 20, the beam shaping assembly 20 is fixedly connected to the support module 60. For example, a threaded hole is provided on the annular formwork 6114, a hole is provided at a corresponding position of the outer wall of the beam shaping assembly 20, and the beam shaping assembly 20 and the annular formwork 6114 are connected by a bolt. It may be understood that another connection manner may be used. Before the concrete is poured, the threaded hole of the annular formwork 6114 is plugged with a plastic protective sleeve to prevent the concrete from leaking from the threaded hole and protect threads. To ensure the compactness of the concrete below the annular formwork, an opening may be provided at a lower portion of the front formwork or the rear formwork, and the concrete is poured from the opening. After the concrete is poured and cured, the plastic protective sleeve plugged in the threaded hole of the annular formwork 6114 is taken out, the beam shaping assembly is placed in an accommodating cavity formed by an inner surface of the annular formwork 6114, and then the beam shaping assembly 20 and the support module 60 are connected by the bolt. It may be understood that the construction may alternatively be carried out in another manner well known to a person skilled in the art.

Figure 5:
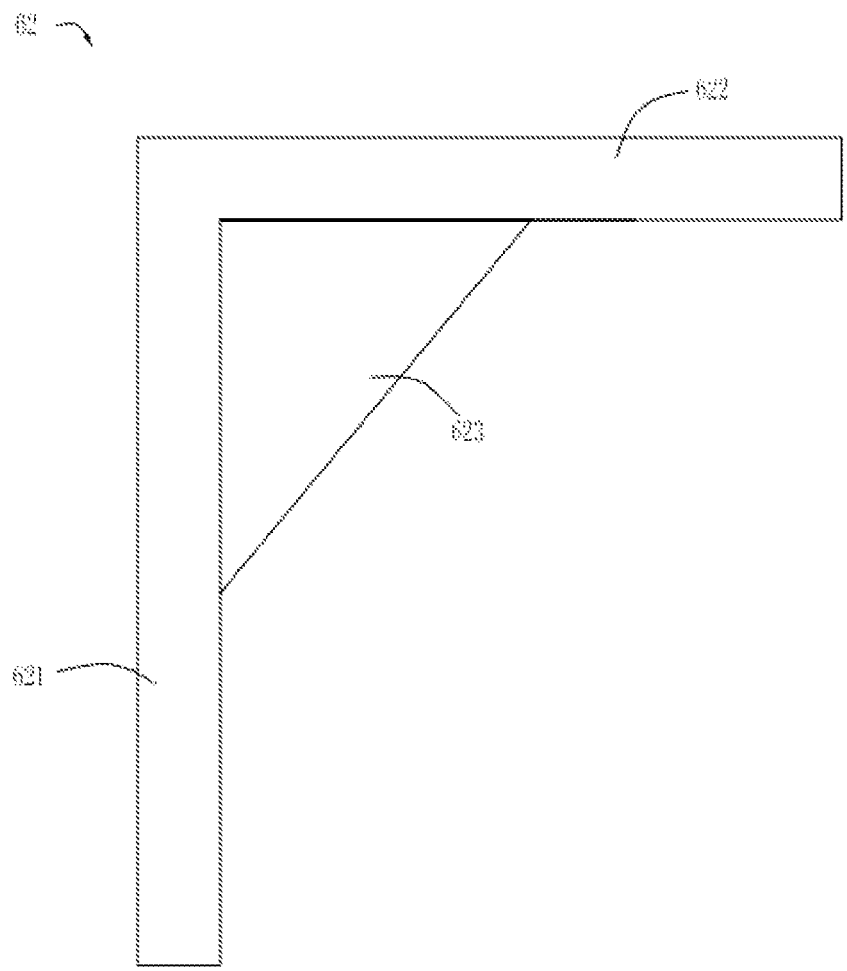
FIG. 5 is a schematic diagram of an adjusting member of a support module of a beam shaping assembly according to an embodiment of the present disclosure.
Figure 6:
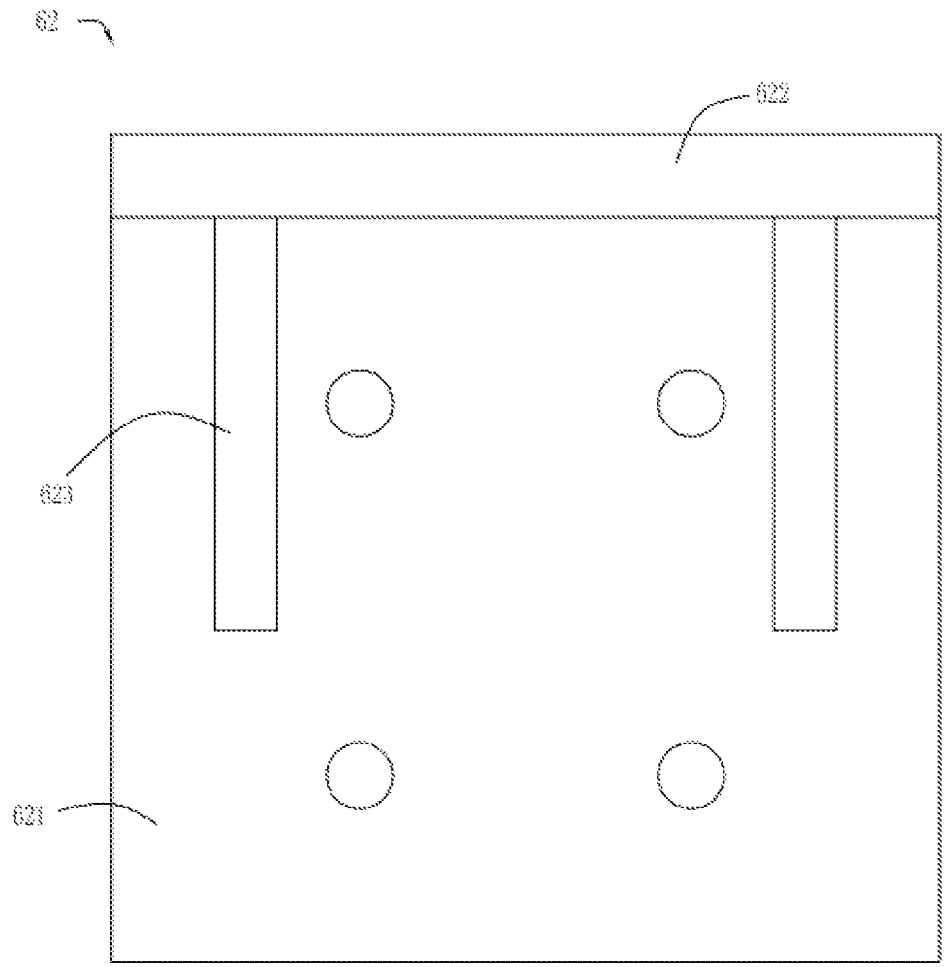
FIG. 6 is a schematic diagram of the adjusting member in FIG. 5 in another direction.

Positions of the support module 60 and the beam shaping assembly 20 are then adjusted. Referring to FIG. 5 and FIG. 6, an adjusting member 62 is disposed on the support module 60, and an adjusting device (not shown in the figure), such as a jack, acts on the adjusting member 62 to adjust the positions of the support module 60 and the beam shaping assembly 20, so that the beam shaping assembly 20 can move between a first position and a second position. A center axis of the beam shaping assembly 20 approximately coincides with a center axis of the transmitting tube of the accelerator at the first position, and the center axis of the beam shaping assembly 20 does not coincide with the center axis of the transmitting tube of the accelerator at the second position. Therefore, a degree of coincidence between the center of the beam shaping assembly and the center of a beam line is improved, so that the target can be placed in a center hole of the beam shaping assembly. The adjusting member 62 is disposed at a lower portion of a side wall of the support module 60 facing the irradiation room 101. It may be understood that the adjusting member 62 may alternatively be disposed at another position. The adjusting member may alternatively be disposed on the beam shaping assembly, and the adjusting member directly drives the beam shaping assembly to adjust a position. Because the jack acts on the adjusting member in the form of a concentrated force, twisted ribs may be disposed at corresponding positions of the reinforcing portion 61 to increase strength. In this embodiment, the adjusting member 62 is an L-shaped support, including a first side plate 621 and a second side plate 622 that are perpendicular to each other. The first side plate 621 is fixed to the lower portion of the side wall of the support module 60 facing the irradiation room 101 by using a bolt. The jack acts on the second side plate 622. The adjusting member 62 further includes a reinforcing rib plate 623 connected to the first side plate and the second side plate to increase strength. The support may be constructed of a steel plate. It may be understood that the support may have another structure or may be made of another material.

After the adjustment, the support module 60 is fixed (for example, a steel plate is disposed in a gap between the support module and the floor, and the support module is fixed to the floor by using a bolt or the like), and a shield (not shown in the figure) is filled between the partition wall 103 and the support module 60 to maintain positions of the support module and the beam shaping assembly and prevent the beam from passing through a gap between the partition wall and the support module. A material of the shield includes at least one of a photon shielding material and a neutron shielding material. The material may be a rigid solid cut into an appropriate size, for example, lead, a lead-antimony alloy, Teflon, graphite, paraffin, PE, PE containing boron carbide or lithium carbonate or lithium fluoride, PMMA (acrylic), or PMMA containing boron carbide or lithium carbonate or lithium fluoride; or may be a powder filled in a rigid container or a flexible container cut into an appropriate size, for example, a powder of boron carbide or lithium carbonate or lithium fluoride; or may be a liquid filled in a rigid container or a flexible container cut into an appropriate size, for example, water that dissolves the powder of boron carbide or lithium carbonate or lithium fluoride, heavy water, and boric acid; or may be a flexible solid, for example, rubber or silicone. The adjusting member 62 may be removed, and then, the shielding plate 70 is mounted to block the shield to further reduce radiation.

The boron neutron capture therapy system 100 may further include a preparation room, a control room, and another space used to assist in treatment. Each irradiation room may be provided with one preparation room used for preparation work, for example, securing an irradiated subject to a treatment table, injecting boron-containing pharmaceuticals, and simulating a treatment plan before treatment with irradiation. A connecting passage may be disposed between the preparation room and the irradiation room, and after the preparation work is completed, the irradiated subject may be directly pushed into the irradiation room or a control mechanism may control automatic entry of the irradiated subject into the irradiation room by a rail. The control room is configured to control the accelerator, the beam transmitting device, the treatment table, and the like, and control and manage the entire irradiation process. A manager may further simultaneously monitor a plurality of the irradiation rooms in the control room.

In this embodiment, the concrete wall is a boron-containing barite concrete wall with the thickness of greater than 1 m and the density of 3 g/c.c. The boron-containing concrete has better neutron absorption property, so that the radiation shielding effect of the concrete is enhanced, and metal materials in the concrete may also be exposed to a smaller amount of neutrons. It should be understood that the concrete wall may have another thickness or density or may be made of another material, and different parts of the concrete wall may have different thicknesses, densities or materials. It should be understood that the present invention may further be applied to other types of neutron irradiation systems; the present invention may also be applied to other types of radiation irradiation systems, and the neutron generating device may be replaced by other radiation generating device, the material of the concrete and supporting assembly may be replaced as needed.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A neutron capture therapy system comprising:
   a neutron generating device for generating a neutron beam;
   a beam shaping assembly for adjusting beam quality of the neutron beam generated by the neutron generating device;
   a concrete wall forming a space for accommodating the neutron generating device and the beam shaping assembly; and
   a support module for supporting a beam shaping assembly and adjusting the position of the beam shaping assembly, wherein the support module comprises concrete and a reinforcing portion at least partially disposed in the concrete, and the support module is disposed in the concrete wall.

2. The neutron capture therapy system according to claim 1, wherein elastic modulus of a material of the reinforcing portion is not less than 40 GPa, ultimate strength of the material is not less than 200 MPa, and yield strength of the material is not less than 100 MPa.

3. The neutron capture therapy system to claim 1, wherein more than 90% of weight of the material of the reinforcing portion is composed of at least one element of C, H, O, N, Si, Al, Mg, Li, B, Mn, Cu, Zn, S, Ca, and Ti.

4. The neutron capture therapy system according to claim 1, wherein half-life of radioactive isotopes generated after the reinforcing portion is activated by neutrons is less than 1 year.

5. The neutron capture therapy system according to claim 1, wherein the reinforcing portion comprises formworks and ribs disposed between the formworks, and the formworks are fixedly connected to the ribs.

6. The neutron capture therapy system according to claim 5, wherein the formworks comprise a lower formwork, a left formwork, a right formwork and an annular formwork, wherein the left formwork and the right formwork are respectively disposed on two sides of the lower formwork, and the annular formwork is surrounded by the lower formwork and the left and right formworks; and the ribs comprise horizontal transverse ribs, horizontal longitudinal ribs, and vertical ribs distributed in the concrete at a preset spacing respectively in a horizontal direction, a vertical direction, and a thickness direction of the concrete.

7. The neutron capture therapy system according to claim 6, wherein the horizontal transverse ribs are welded and anchored to the left formwork, the right formwork, and the annular formwork, the vertical ribs are welded and anchored to the lower formwork, the annular formwork, and the horizontal transverse ribs, and the horizontal longitudinal ribs are welded and anchored to the horizontal transverse ribs and the vertical ribs.

8. The neutron capture therapy system according to claim 6, wherein an outer wall of the beam shaping assembly fits an inner surface of the annular formwork, and the beam shaping assembly is fixedly connected to the support module.

9. A neutron capture therapy system comprising:
a neutron generating device comprising an accelerator and a target, wherein a charged particle beam generated by acceleration of the accelerator acts with the target to generate a neutron beam;
a beam shaping assembly comprising:
a moderator configured to moderate the neutrons generated from the target to an epithermal neutron energy range,
a reflector surrounding the moderator, wherein the reflector directs deviating neutrons back to the moderator to enhance intensity of an epithermal neutron beam,
a thermal neutron absorber provided to absorb thermal neutrons to avoid overdosing in superficial normal tissues during treatment,
a radiation shield provided to shield leaking neutrons and photons so as to reduce dose to normal tissues in a non-irradiation area, and
a beam exit;
a concrete wall forming a space for accommodating the neutron generating device and the beam shaping assembly; and
a support module comprises concrete and a reinforcing portion at least partially disposed in the concrete, wherein the support module is disposed in the concrete wall, and the support module is provided to support the beam shaping assembly and adjust the position of the beam shaping assembly.

10. The neutron capture therapy system according to claim 9, wherein the neutron capture therapy system further comprises an irradiation room and a charged particle beam generation room, the irradiation room and the charged particle beam generation room are spaces formed by the concrete wall, the neutron capture therapy system comprises a treatment table disposed in the irradiation room, an irradiated subject on the treatment table is treated with irradiation of the neutron beam in the irradiation room, the charged particle beam generation room at least partially accommodates the accelerator, and the support module and the beam shaping assembly are at least partially accommodated in a partition wall between the irradiation room and the charged particle beam generation room.

11. The neutron capture therapy system according to claim 10, wherein the partition wall is provided, on a side close to the irradiation room, with an accommodating groove at least partially accommodating the support module, and is provided, on a side close to the charged particle beam generation room, with a groove for a transmitting tube of the accelerator to pass through, the accommodating groove and the groove run through the partition wall in a transmission direction of the neutron beam, and a cross section contour of the support module is located between cross section contours of the accommodating groove and the groove on a plane perpendicular to the transmission direction of the neutron beam.

12. The neutron capture therapy system according to claim 10, wherein an adjusting member is disposed on the support module to adjust positions of the support module and the beam shaping assembly, wherein the beam shaping assembly moves between a first position and a second position, the accelerator comprises a transmitting tube, a center axis of the beam shaping assembly approximately coincides with a center axis of the transmitting tube at the first position, and the center axis of the beam shaping assembly does not coincide with the center axis of the transmitting tube at the second position.

13. The neutron capture therapy system according to claim 12, wherein the adjusting member comprises a first side plate and a second side plate that are connected to each other, the first side plate is fixedly and detachably connected to the support module, and the second side plate is provided to act on.

14. The neutron capture therapy system according to claim 12, wherein a shield is filled between the partition wall and the support module to maintain positions of the support module and the beam shaping assembly, a material of the shield comprises at least one of a photon shielding material and a neutron shielding material, and the shield comprises at least one of a rigid solid, a flexible solid, a liquid, and a powder.

15. The neutron capture therapy system according to claim 10, wherein a shielding plate is disposed on the side of the partition wall close to the irradiation room, and the shielding plate matches a cross section contour of the support module on a plane perpendicular to the transmission direction of the neutron beam.

16. A neutron capture therapy system comprising:
a neutron generating device comprising an accelerator and a target, wherein a charged particle beam generated by acceleration of the accelerator acts with the target to generate a neutron beam;
a beam shaping assembly comprising:
a moderator configured to moderate the neutrons generated from the target to an epithermal neutron energy range, a reflector surrounding the moderator, wherein the reflector directs deviating neutrons back to the moderator to enhance intensity of an epithermal neutron beam, a thermal neutron absorber provided to absorb thermal neutrons to avoid overdosing in superficial normal tissues during treatment, a radiation shield provided to shield leaking neutrons and photons so as to reduce dose to normal tissues in a non-irradiation area, and a beam exit;

a concrete wall forming a space for accommodating the neutron generating device and the beam shaping assembly;

a support module comprises concrete and a reinforcing portion at least partially disposed in the concrete, wherein the support module is disposed in the concrete wall and provided to support the beam shaping assembly; and an adjusting member configured to adjust position of the beam shaping assembly.

17. The neutron capture therapy system according to claim 16, wherein the beam shaping assembly moves between a first position and a second position, the accelerator comprises a transmitting tube, a center axis of the beam shaping assembly approximately coincides with a center axis of the transmitting tube at the first position, and the center axis of the beam shaping assembly does not coincide with the center axis of the transmitting tube at the second position.

18. The neutron capture therapy system according to claim 16, wherein the adjusting member comprises a first side plate and a second side plate that are connected to each other, the first side plate is fixedly and detachably connected to the support module or the beam shaping assembly, and the second side plate is provided to act on.

19. The neutron capture therapy system according to claim 16, wherein the adjusting member is disposed on the support module to adjust positions of the support module and the beam shaping assembly.

20. The neutron capture therapy system according to claim 19, wherein a shield is filled between the concrete wall and the support module to maintain positions of the support module and the beam shaping assembly, a material of the shield comprises at least one of a photon shielding material and a neutron shielding material, and the shield comprises at least one of a rigid solid, a flexible solid, a liquid, and a powder.

* * * * *